US 6,524,275 B1

(12) United States Patent
Lynch et al.

(10) Patent No.: US 6,524,275 B1
(45) Date of Patent: Feb. 25, 2003

(54) INFLATABLE DEVICE AND METHOD FOR TREATING GLAUCOMA

(75) Inventors: Mary G. Lynch, Atlanta, GA (US); Reay H. Brown, Atlanta, GA (US)

(73) Assignee: GMP Vision Solutions, Inc., Ft. Lauderdale, FL (US)

(*) Notice: Subject to any disclaimer, the term of this patent is extended or adjusted under 35 U.S.C. 154(b) by 0 days.

(21) Appl. No.: 09/558,557

(22) Filed: Apr. 26, 2000

Related U.S. Application Data
(60) Provisional application No. 60/131,030, filed on Apr. 26, 1999.

(51) Int. Cl.[7] ............................................... A61M 25/10
(52) U.S. Cl. ..................... 604/96.01; 604/264; 604/528
(58) Field of Search .................. 604/93.01, 95.04, 604/96.01, 264, 523, 528, 537, 539

(56) References Cited

U.S. PATENT DOCUMENTS

| | | | |
|---|---|---|---|
| 4,037,604 A | 7/1977 | Newkirk | 128/350 V |
| 4,299,227 A | 11/1981 | Lincoff | 128/344 |
| 4,402,681 A | 9/1983 | Haas et al. | 604/9 |
| 4,428,746 A | 1/1984 | Mendez | 604/8 |
| 4,521,210 A | 6/1985 | Wong | 604/8 |
| 4,634,418 A | 1/1987 | Binder | 604/8 |
| 4,750,901 A | 6/1988 | Molteno | 604/8 |
| 4,787,885 A | 11/1988 | Binder | 604/8 |
| 4,867,173 A | * 9/1989 | Leoni | 600/585 |
| 4,886,488 A | 12/1989 | White | 604/9 |

(List continued on next page.)

FOREIGN PATENT DOCUMENTS

| | | |
|---|---|---|
| CA | 2244646 | 2/1999 |
| CH | 92111244 | 7/1993 |
| DE | 198 40 047 A | 3/2000 |
| EP | 0 858 788 A | 8/1998 |
| EP | 0 898 947 A2 | 3/1999 |
| FR | 2710269 | 3/1995 |
| JP | HEI 11-123205 | 5/1999 |
| WO | WO 98/23237 | 6/1998 |
| WO | WO 98/30181 | 7/1998 |
| WO | WO 98/35639 | 8/1998 |

(List continued on next page.)

OTHER PUBLICATIONS

Shields, M. Bruce, *Textbook of Glaucoma*, Fourth Ed., Williams & Wilkins Publishers, 1998, pp. 5–31.
*Biomedical Foundations of Ophthalmology*, vol. 1, Harper & Row Publishers, 1983, pp. 1–74.
Buskirk, E. Michael et al., "Lens Depression and Aqueous Outflow in Enucleated Primate Eyes", American Journal of Ophthamology, vol. 76, No. 5, Nov. 1973, pp. 632–640.
Buskirk, E. Michael, "Trabeculotomy in the immature, enucleated human eye", Invest. Ophthalmol. Visual Sci., vol. 6, No. 1, Jan. 1977, pp. 63–66.
Moses, Robert A. et al., "Blood Reflux in Schlemm's Canal", Arch Ophthamol., vol. 97, Jul. 1979, pp. 1307–1310.
Fine, Ben S., et al., "A Clinicopathologic Study of Four Cases of Primary Open–Angle Glaucoma Compared to Normal Eyes", American Journal of Ophthalmology, vol. 91, No. 1, 1981, pp. 88–105.
Grierson, I., et al., "Age–related Changes in the Canal of Schlemm", Exp. Eye Res., (1984) 39, pp. 505–512.

(List continued on next page.)

Primary Examiner—Edward K. Look
Assistant Examiner—Richard A. Edgar
(74) Attorney, Agent, or Firm—Sutherland, Asbill & Brennan, LLP

(57) ABSTRACT

Catheter devices and methods for treating glaucoma and other eye diseases by expandable dilatation of Schlemm's canal and/or direct injection of medications into Schlemm's canal.

18 Claims, 5 Drawing Sheets

U.S. PATENT DOCUMENTS

| | | | |
|---|---|---|---|
| 4,936,825 A | 6/1990 | Ungerleider | 604/8 |
| 4,946,436 A | 8/1990 | Smith | 604/8 |
| 4,968,296 A | 11/1990 | Ritch et al. | 604/8 |
| 5,041,081 A | 8/1991 | Odrich | 604/9 |
| 5,073,163 A | 12/1991 | Lippman | 604/9 |
| 5,092,837 A | 3/1992 | Ritch et al. | 604/8 |
| 5,127,901 A | 7/1992 | Odrich | 604/9 |
| 5,178,604 A | 1/1993 | Baerveldt et al. | 604/8 |
| 5,180,362 A | 1/1993 | Worst | 604/8 |
| 5,300,020 A | 4/1994 | L'Esperance, Jr. | 604/9 |
| 5,318,513 A | 6/1994 | Leib et al. | 604/8 |
| 5,334,137 A | 8/1994 | Freeman | 604/8 |
| 5,338,291 A | 8/1994 | Speckman et al. | 604/9 |
| 5,346,464 A | 9/1994 | Camras | 604/9 |
| 5,360,399 A | 11/1994 | Stegmann | 604/49 |
| 5,364,374 A | 11/1994 | Morrison et al. | 604/272 |
| 5,370,607 A | 12/1994 | Memmen | 604/8 |
| 5,370,641 A | 12/1994 | O'Donnell, Jr. | 606/4 |
| 5,372,577 A | 12/1994 | Ungerleider | 604/8 |
| 5,397,300 A | 3/1995 | Baerveldt et al. | 604/8 |
| 5,433,701 A | 7/1995 | Rubinstein | 604/8 |
| 5,454,796 A | 10/1995 | Krupin | 604/294 |
| 5,476,445 A | 12/1995 | Baerveldt et al. | 604/8 |
| 5,486,165 A | 1/1996 | Stegmann | 604/8 X |
| 5,558,629 A | 9/1996 | Baerveldt et al. | 604/93 X |
| RE35,390 E | 12/1996 | Smith | 604/8 |
| 5,601,094 A | 2/1997 | Reiss | 604/8 X |
| 5,626,558 A | 5/1997 | Suson | 604/8 |
| 5,626,559 A | 5/1997 | Solomon | 604/9 |
| 5,681,275 A | 10/1997 | Ahmed | 604/9 |
| 5,702,414 A | 12/1997 | Richter et al. | 606/166 |
| 5,704,907 A | 1/1998 | Nordquist et al. | 604/8 |
| 5,713,844 A | 2/1998 | Peyman | 604/9 |
| 5,723,005 A | 3/1998 | Herrick | 604/8 X |
| 5,743,868 A | 4/1998 | Brown et al. | 604/8 |
| 5,752,928 A | 5/1998 | de Roulhac et al. | 604/8 |
| 5,766,243 A | 6/1998 | Christensen et al. | 623/4 |
| 5,785,674 A | 7/1998 | Mateen | 604/9 |
| 5,807,302 A | 9/1998 | Wandel | 604/8 |
| 5,830,171 A | 11/1998 | Wallace | 604/8 |
| 5,865,831 A | 2/1999 | Cozean et al. | 606/6 |
| 5,868,697 A | 2/1999 | Richter et al. | 604/8 |
| 5,879,319 A | 3/1999 | Pynson et al. | 604/8 |
| 5,882,327 A | 3/1999 | Jacob | 604/8 |
| 5,891,084 A | 4/1999 | Lee | 604/54 |
| 5,893,837 A | 4/1999 | Eagles et al. | 604/9 |
| 5,968,058 A | 10/1999 | Richter et al. | 606/166 |
| 6,050,970 A | 4/2000 | Baerveldt | 604/28 |
| 6,063,116 A | 5/2000 | Kelleher | 623/4 |
| 6,063,396 A | 5/2000 | Kelleher | 424/428 |
| 6,077,299 A | 6/2000 | Adelberg et al. | 604/9 X |
| 6,102,045 A | 8/2000 | Nordquist et al. | 604/8 X |
| 6,142,990 A * | 11/2000 | Burk | 606/17 |
| 6,168,575 B1 | 1/2001 | Soltanpour | 604/9 |
| 6,193,656 B1 | 2/2001 | Jeffries et al. | 600/398 |
| 6,197,056 B1 | 3/2001 | Schachar | 623/4.1 |
| 6,375,642 B1 | 4/2002 | Grieshaber et al. | 604/294 |
| 6,413,245 B1 * | 7/2002 | Yaacobi et al. | 604/264 |
| 2002/0026200 A1 * | 2/2002 | Savage | 606/108 |

FOREIGN PATENT DOCUMENTS

| | | |
|---|---|---|
| WO | WO 99/26567 | 6/1999 |
| WO | WO 99/38470 | 8/1999 |
| WO | WO 00/13627 | 3/2000 |
| WO | WO 01/78631 | 10/2001 |
| WO | WO 01/78656 | 10/2001 |

OTHER PUBLICATIONS

McMenamin, Paul G., et al., "Age–related Changes in the Human Outflow Apparatus", Ophthalmology, vol. 93, No. 2., Feb. 1986, pp. 194–209.

Demailly, P., et al., "Non–penetrating deep sclerectomy combined with a collagen implant in primary open–angle glaucoma. Medium–term retrospective results", J. Fr. Ophthalmol., vol. 19, No. 11, 1996, pp. 659–666. (Abstract only).

*Glaucoma—Basic and Clinical Science Course*, Section 10, Chapter 11, 1998–1999, American Academy of Ophthalmology, p. 9.

Welsh, N.H., et al., "The 'deroofing' of Schlemm's canal in patients with open–angle glaucoma through placement of a collagen drainage device", Ophthalmic Surg. Lasers, vol. 29, No. 3, Mar. 1998, pp. 216–226, (abstract only).

Karlen, M.E., et al., "Deep sclerectomy with collagen implant: medium term results", Br. J. Ophthalmol. vol. 83, No. 1, Jan. 1999, pp. 6–11, (abstract only).

Hamard, P., et al., "Deep nonpenetrating sclerectomy and open angle glaucoma. Intermediate results from the first operated patients", J. Fr. Ophtalmol., vol. 22 (j), Feb. 1999, pp. 25–31, (abstract only).

Mermoud, A., et al., "Comparison of deep sclerectomy with collagen implant and trabeculectomy in open–angle glaucoma", J. Cataracat Refract. Surg., vol. 25, No. 3, Mar. 1999, pp. 323–331, (abstract only).

Spiegel, Detlev, et al., "Schlemm's Canal Implant: A New Method to Lower Intraocular Pressure in Patients with POAG", Ophthalmic Surgery and Lasers, vol. 30, No. 6, Jun. 1999, pp. 492–494.

Johnson, M.C., et al, "The Role of Schlemm's Canal in Aqueous Outflow from the Human Eye", Investigative Ophthalmology & Visual Science, vol. 24, No. 3, Mar. 1983, pp. 320–325.

Wilson, Ellen D., "Implants offer choices for glaucoma surgeons", EW Glaucoma, Oct. 11, 1999, website "http://www.eyeorld.org/sep99/999p60.asp".

"Improving the flow: A survey of available implants", EW Practice Management, Oct. 11, 1999, website "http://www.eyeworld.org/tooltime/999inserts.asp".

Samalonis, Lisa B., "New Horizons in the surgical treatment of glaucoma", EW Glaucoma, Oct. 11, 1999, website "http://www.eyeworld,org/sep99/999p62.asp".

U.S. Clinical Wick Trials, Oct. 11, 1999, website http://www.cornea.org/us.htm.

Allingham, R.R., et al., "Morphometric Analysis of Schlemm's Canal in Normal and Glaucomatous Human Eyes", Glaucoma Paper Presentation, (abstract only—not dated).

Robinson, James C., et al., "Superior Cervical Ganglionectomy: Effects on Aqueous Human FLow in the Cynomolgus Monkey", Glaucoma Paper Presentation, (abstract only—not dated).

Gharagozloo, N. Ziai, et al., "Unilateral exfoliation syndrome without glaucoma—a comparison of aqueous dynamica between affected and normal eyes", Glaucoma Paper Presentation, (abstract only—not dated).

Moses, Robert A., "Circumferential Flow in Schlemm's Canal", American Journal of Ophthalmology, vol. 88, No. 3, Part II, Sep. 1979, pp. 585–591.

Spiegel, D., "Surgical Glaucoma Therapy" in Benefits and Risks of Ophthalmological Therapy (Kampik & Grehn, Eds.) Ch. 7 (Germany 1998).

\* cited by examiner

INFLATABLE DEVICE AND METHOD FOR TREATING GLAUCOMA

CROSS-REFERENCE TO RELATED APPLICATIONS

This application claims the benefit of U.S. Provisional Application No. 60/131,030, filed Apr. 26, 1999.

TECHNICAL FIELD

The present invention is generally directed to a surgical treatment for glaucoma and other eye diseases and relates more particularly to an inflatable device and method for use in ophthalmic surgery to mechanically dilate Schlemm's canal in the eye and/or instill medications within Schlemm's canal for direct action upon the canal, the trabecular meshwork, and adjacent tissues.

BACKGROUND OF THE INVENTION

Glaucoma is a significant public health problem, because glaucoma is a major cause of blindness. The blindness that results from glaucoma involves both central and peripheral vision and has a major impact on an individual's ability to lead an independent life.

Glaucoma is an optic neuropathy (a disorder of the optic nerve) that usually occurs in the setting of an elevated intraocular pressure. The pressure within the eye increases and this is associated with changes in the appearance ("cupping") and function ("blind spots" in the visual field) of the optic nerve. If the pressure remains high enough for a long enough period of time, total vision loss occurs. High pressure develops in an eye because of an internal fluid imbalance.

The eye is a hollow structure that contains a clear fluid called "aqueous humor." Aqueous humor is formed in the posterior chamber of the eye by the ciliary body at a rate of about 2.5 microliters per minute. The fluid, which is made at a fairly constant rate, then passes around the lens, through the pupillary opening in the iris and into the anterior chamber of the eye. Once in the anterior chamber, the fluid drains out of the eye through two different routes. In the "uveoscleral" route, the fluid percolates between muscle fibers of the ciliary body. This route accounts for ten percent of the aqueous outflow. The primary pathway for aqueous outflow is through the "canalicular" route that involves the trabecular meshwork and Schlemm's canal.

The trabecular meshwork and Schlemm's canal are located at the junction between the iris and the sclera. This junction or corner is called "the angle." The trabecular meshwork is a wedge-shaped structure that runs around the circumference of the eye. It is composed of collagen beams arranged in a three-dimensional sieve-like structure. The beams are lined with a monolayer of cells called trabecular cells. The spaces between the collagen beams are filled with an extracellular substance that is produced by the trabecular cells. These cells also produce enzymes that degrade the extracellular material. Schlemm's canal is adjacent to the trabecular meshwork. The outer wall of the trabecular meshwork coincides with the inner wall of Schlemm's canal. Schlemm's canal is a tube-like structure that runs around the circumference of the cornea. In human adults, Schlemm's canal is believed to be divided by septa into a series of autonomous, dead-end canals.

The aqueous fluid travels through the spaces between the trabecular beams, across the inner wall of Schlemm's canal into the canal, through a series of collecting channels that drain from Schlemm's canal and into the episcleral venous system. In a normal situation, aqueous production is equal to aqueous outflow and intraocular pressure remains fairly constant in the 15 to 21 mm Hg range. In glaucoma, the resistance through the canalicular outflow system is abnormally high.

In primary open angle glaucoma, which is the most common form of glaucoma, the abnormal resistance is believed to be along the outer aspect of trabecular meshwork and the inner wall of Schlemm's canal. It is believed that an abnormal metabolism of the trabecular cells leads to an excessive build up of extracellular materials or a build up of abnormally "stiff" materials in this area. Primary open angle glaucoma accounts for approximately eighty-five percent of all glaucoma. Other forms of glaucoma (such as angle closure glaucoma and secondary glaucomas) also involve decreased outflow through the canalicular pathway but the increased resistance is from other causes such as mechanical blockage, inflammatory debris, cellular blockage, etc.

With the increased resistance, the aqueous fluid builds up because it cannot exit fast enough. As the fluid builds up, the intraocular pressure (IOP) within the eye increases. The increased IOP may compromise the vascular supply to the optic nerve that carries vision from the eye to the brain. Some optic nerves seem more susceptible to IOP than other eyes. While research is investigating ways to protect the nerve from an elevated pressure, the only therapeutic approach currently available in glaucoma is to reduce the intraocular pressure.

The clinical treatment of glaucoma is approached in a step-wise fashion. Medication often is the first treatment option. Administered either topically or orally, these medications work to either reduce aqueous production or they act to increase outflow. Currently available medications have many serious side effects including: congestive heart failure, respiratory distress, hypertension, depression, renal stones, aplastic anemia, sexual dysfunction and death. Compliance with medication is a major problem, with estimates that over half of glaucoma patients do not follow their correct dosing schedules.

When medication fails to adequately reduce the pressure, laser trabeculoplasty often is performed. In laser trabeculoplasty, thermal energy from a laser is applied to a number of noncontiguous spots in the trabecular meshwork. It is believed that the laser energy stimulates the metabolism of the trabecular cells in some way, and changes the extracellular material in the trabecular meshwork. In approximately eighty percent of patients, aqueous outflow is enhanced and IOP decreases. However, the effect often is not long lasting and fifty percent of patients develop an elevated pressure within five years. The laser surgery is not usually repeatable. In addition, laser trabeculoplasty is not an effective treatment for primary open angle glaucoma in patients less than fifty years of age, nor is it effective for angle closure glaucoma and many secondary glaucomas.

If laser trabeculoplasty does not reduce the pressure enough, then filtering surgery is performed. With filtering surgery, a hole is made in the sclera and angle region. This hole allows the aqueous fluid to leave the eye through an alternate route.

The most commonly performed filtering procedure is a trabeculectomy. In a trabeculectomy, a posterior incision is made in the conjunctiva, the transparent tissue that covers the sclera. The conjunctiva is rolled forward, exposing the sclera at the limbus. A partial thickness scleral flap is made and dissected half-thickness into the cornea. The anterior chamber is entered beneath the scleral flap and a section of deep sclera and trabecular meshwork is excised. The scleral flap is loosely sewn back into place. The conjunctival incision is tightly closed. Post-operatively, the aqueous fluid passes through the hole, beneath the scleral flap and collects in an elevated space beneath the conjunctiva. The fluid then is either absorbed through blood vessels in the conjunctiva or traverses across the conjunctiva into the tear film.

Trabeculectomy is associated with many problems. Fibroblasts that are present in the episclera proliferate and migrate and can scar down the scleral flap. Failure from scarring may occur, particularly in children and young adults. Of eyes that have an initially successful trabeculectomy, eighty percent will fail from scarring within three to five years after surgery. To minimize fibrosis, surgeons now are applying antifibrotic agents such as mitomycin C (MMC) and 5-fluorouracil (5-FU) to the scleral flap at the time of surgery. The use of these agents has increased the success rate of trabeculectomy but also has increased the prevalence of hypotony. Hypotony is a problem that develops when aqueous flows out of the eye too fast. The eye pressure drops too low (usually less than 6.0 mmHg); the structure of the eye collapses and vision decreases.

An alternative surgical method for glaucoma management can be directed more specifally at Schlemm's canal. U.S. Pat. No. 5,360,399 teaches the placement of part of a plastic or steel tube into Schlemm's canal with injection of a viscous material through holes in the tube to hydraulically hydrodissect the trabecular meshwork. However, the '399 device provides little or no option for the distance of the hydrodissection within the length of Schlemm's canal, nor suggests a means for dilating the canal to facilitate the natural drainage therefrom.

A need exists, then, for a system that would allow for precise dilation and expansion of Schlemm's canal along any portion thereof. A need exists for the selective, direct delivery of therapeutic agents into Schlemm's canal that provides more effective control of glaucoma with fewer systemic complications than with existing medication delivery alternatives. In addition, a more physiologic system is needed to enhance the drainage of aqueous fluid into Schlemm's canal from the anterior chamber angle. Enhancing aqueous flow directly into Schlemm's canal would minimize scarring since the angle region is populated with a single line of nonproliferating trabecular cells. Enhancing aqueous flow directly into Schlemm's canal and naturally therefrom into the collecting channels would minimize hypotony since the canal is part of the normal outflow system and is biologically engineered to handle the normal volume of aqueous humor. Enhancing aqueous flow directly into Schlemm's canal would eliminate complications such as endophthalmitis, hypotony, and leaks.

SUMMARY OF THE INVENTION

The present invention is directed to a novel inflatable catheter device and an associated method for the surgical correction of glaucoma in which the inventive device is placed within Schlemm's canal and the inflatable element of the device is expanded to temporarily stretch and expand the lumen of the canal. At that point, the inflatable element may be used to temporarily occlude outflow through the canal, while physiologic material is injected through another lumen of the device, thereby distending the canal and expanding areas of stenosis within the canal. The inflated element may be decompressed and removed after the desired expansion is achieved, or the device may be extracted with the inflatable component expanded, to further mechanically dilate the passageway within Schlemm's canal.

The present invention may also be employed to inject various medications directly within Schlemm's canal. Such medications may include, but are not limited to, antifibrotics, antibiotics, and other medications which may have direct effects within the internal structures of Schlemm's canal, the trabecular meshwork, and other tissues of the eye.

The present invention may also be employed to deploy various stents or shunts directly within Schlemm's canal to help maintain patency within the canal following removal of the inflatable device.

The inventive device and method described herein therefore facilitates the normal physiologic pathway for drainage of aqueous humor from the anterior chamber to Schlemm's canal and exiting to the collecting channels, rather than shunting to the sclera or another anatomic site as is done in most prior art devices. In addition, the present invention provides a mechanism for the delivery of devices or medications directly into Schlemm's canal and the adjacent ophthalmic anatomy.

BRIEF DESCRIPTION OF THE DRAWINGS

FIG. 1 further shows a guidewire which extends throughout the length of said catheter.

DETAILED DESCRIPTION OF PRESENT INVENTION

Figure 1:
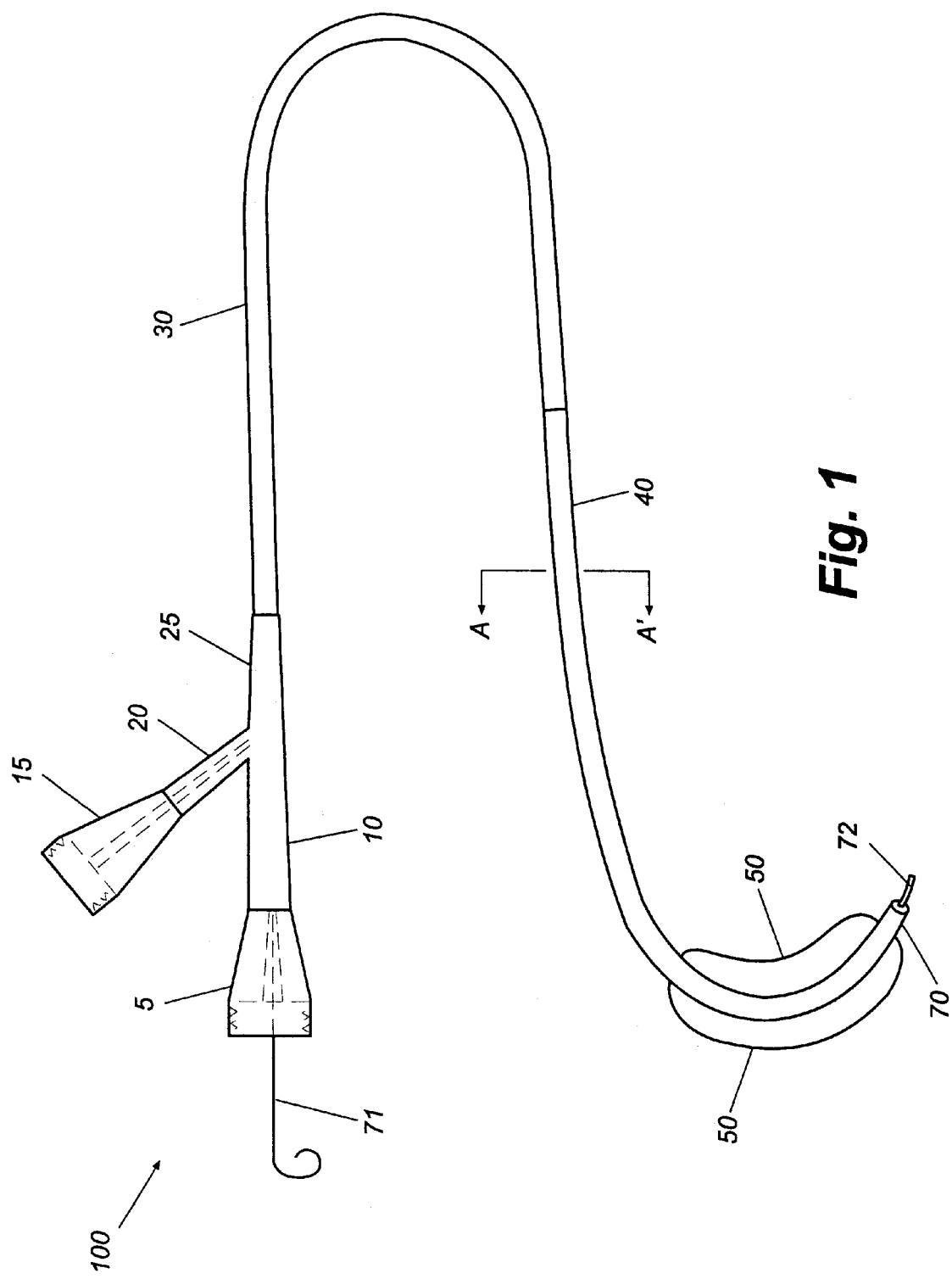
FIG. 1 is an illustration showing an overall view of one embodiment of the present invention, in which the inventive device is comprised of a dual, concentric lumen catheter with an outer lumen terminating in an inflatable sleeve, and an inner lumen which protrudes distal to the inflatable sleeve and terminates in an open tip.

The present invention provides catheter devices for the dilatation of Schlemm's canal of the eye by mechanically distending a portion of the canal when inflated. The inflatable catheter devices may also be used to provide a conduit capable of delivering therapeutic and/or expansive medicaments injected therethrough into Schlemmn's canal. The inflatable catheter devices may also be used to provide a delivery mechanism for stents, shunts and the like into Schlemm's canal to maintain patency within the canal to facilitate the natural drainage of aqueous humor. Furthermore, optical fibers, cameras, temperature sensors, pressure sensors, and any other probe or suitable useful device can be delivered to within Schlemmn's canal by the present invention.

The invention provides a catheter device comprising a proximal portion manually controllable by a user, and a distal portion shaped and sized for circumferential insertion into a portion of Schlemm's canal. The device further comprises an inflation supply lumen extending from the proximal portion to the distal portion. The distal portion of the inflation supply lumen can be constructed of a resilient, expandable material for radially dilating a portion of Schlemm's canal when inflated. Inflation can be achieved by gas or liquid injection into the proximal portion of the inflation supply lumen, and can be carefully monitored for volume and pressure so as to accurately expand the distal lumen of the catheter device to the desired amount. Therefore, the distal portion of the inflationary lumen can move between a first insertion position and a second inflation position when inflated via the proximal portion.

It has not been heretofore determined that Schlemm's canal is patent throughout its circumference in normal individuals, as opposed to being divided by septa into multiple dead end canals. The invention utilizes this new knowledge to access Schlemm's canal and to create and maintain patency within the canal with the present devices.

The proximal portion of the catheter device is designed to receive a connector for attachment of an inflation means, such as an injection syringe or pump. The device can also comprise a guiding lumen extending from the proximal portion to the distal portion, wherein the guiding lumen contains a steerable guidewire for directing the catheter device into a desired length of Schlemm's canal.

In some embodiments, the catheter device can provide medicinal compositions therethrough for deposit into Schlemm's canal. This can be achieved by utilizing a single lumen with one or more openings or fenestrations in the distal portion thereof. In some cases, the delivery of a medicament may itself be an inert material, such as a gel, to expand and dilate the canal sufficiently, thereby providing a therapeutic effect. Alternatively, the catheter device can have a separate medicament delivery lumen and an inflation lumen, as described above. In certain embodiments, the inflation lumen is concentrically located at a site along the distal portion to provide occlusion of Schlemm's canal either distally or proximally to the material injected.

The present invention is directed to devices and surgical methods for dilating Schlemm's canal and/or for delivering topically active medications directly into Schlemm's canal utilizing an inflatable device that is surgically inserted within at least a portion of Schlemm's canal. The portion of the device extending circumferentially into Schlemm's canal may be fashioned from a flexible, biologically inert material. The distal portion of the catheter device has a diameter approximately equal to that of Schlemm's canal of a human eye. The external diameter of the distal portion can be between about 0.1 and 0.5 mm, or preferably about 0.3 mm. The length of the distal portion can be between about 1.0 and 20 mm, or preferably about 10 mm. The distal portion of the catheter device can have a pre-formed curve having a radius approximately equal to that of Schlemm's canal. The radius of the distal portion can be between about 3 and 10 mm, or preferably about 6 mm.

One embodiment of the present invention is illustrated in FIG. 1, in which the catheter device 100 is shown in a side view. The catheter device 100 is comprised of two portions, a proximal portion 30 which joins one or more distal portions 40. The proximal portion 30 is tubular, containing one or more lumens in either a concentric or parallel internal configuration. In the exemplary embodiment of the present invention, the proximal portion 30 is constructed of a biologically inert, flexible material such as silicone or similar polymers. Alternate materials might include, but are not limited to, thin-walled Teflon, polypropylene, or other polymers or plastics.

At its proximal end, the proximal portion 30 is attached to a connector 25 which provides fluid communication between one or more lumens within the proximal portion 30 and standard connectors for medical syringe attachment. In the exemplary embodiment of the present invention, the connector provides such communication with separate subconnectors 10 and 20. Subconnector 10 terminally connects to syringe attachment 5, which provides a connection for a syringe [not shown] used to inject materials into one or more communicating lumens within the proximal portion 30. Subconnector 20 terminally connects to syringe attachment 15, which provides a connection for a syringe [not shown] used to inject materials into one or more communicating lumens within the proximal portion 30. Subconnector 10 may also allow passage therethrough for a guidewire 71 with a blunted tip 72.

The proximal portion 30 of the catheter connects with the distal portion 40. The lumen(s) of the proximal portion 30 each connect with a corresponding lumen within the distal portion 40. The distal portion 40 is sized and shaped to be received within Schlemm's canal in the eye. In an alternate embodiment, the distal portion 40 may be a continuous, tapering extension of the proximal portion 30. The distal portion 40 terminates in a tip 70 which may be tapered and/or blunted, and may be open or closed. In the embodiment shown in FIG. 1, the distal tip of the guidewire 72 extends slightly beyond the tip 70 of the distal portion 40 of the device. In the embodiment shown in FIG. 1, the distal portion has a concentric inflatable sleeve 50. In an alternate embodiment, distal to the inflatable sleeve 50, the distal portion 40 may continue as a fenestrated catheter 60, containing one or more fenestrations 65.

Figure 2:
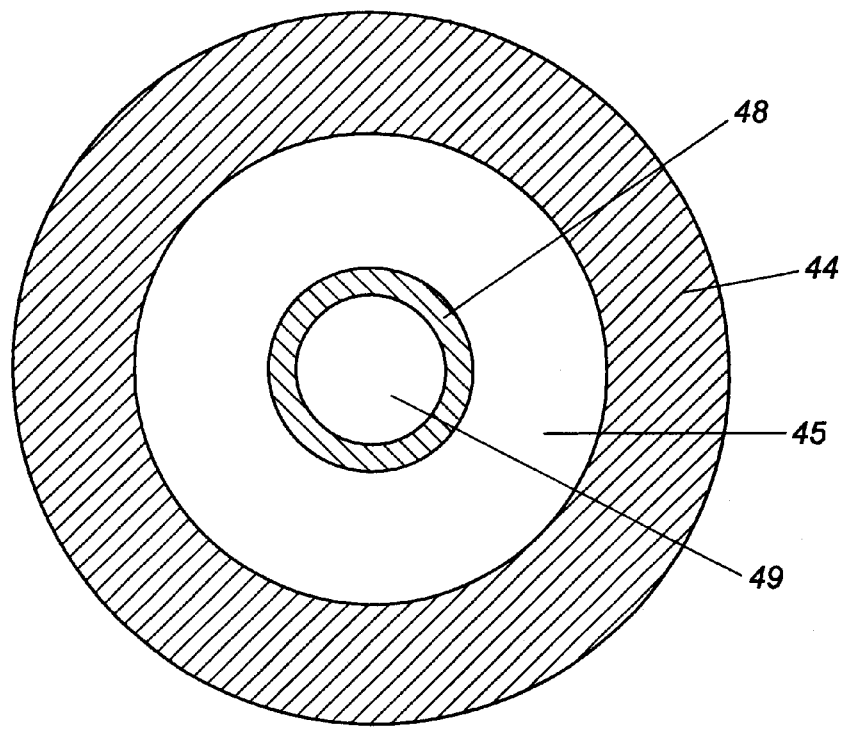
FIG. 2 is an illustration showing a cross sectional view at point A—A' as shown on FIG. 1 and detailing the concentric nature of the two lumens within this embodiment of the present invention.

FIG. 2 shows a cross section at point A—A' through the embodiment of the present invention as indicated in FIG. 1. In this embodiment, a concentric, dual lumen catheter is provided, with an outer tube 44 and an inner tube 48. An outer tube lumen 45 is defined between the walls of the outer tube 44 and the inner tube 48. An inner tube lumen 49 is present within the inner tube 48.

Figure 3:
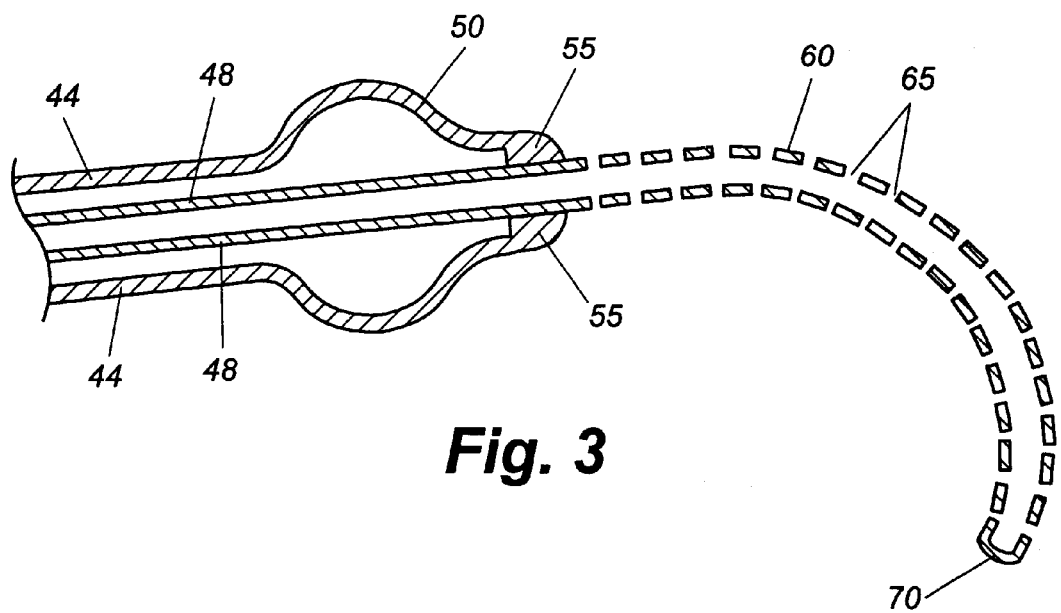
FIG. 3 is an illustration showing a detail of the distal portion of one embodiment of the present invention in which the inventive catheter is configured with the inflatable sleeve operated by the external lumen, and with the internal lumen protruding distally to the inflatable sleeve and containing a plurality of fenestrations before terminating in a blunted tip.

A longitudinal cross-section detailing the terminal aspect of the distal portion 40 in this embodiment of the present invention is shown in FIG. 3. In this embodiment, the outer tube 44 is continuous with the inflatable sleeve 50, and the outer tube 44 terminates in a sealed end 55 at the distal end of the inflatable sleeve 50. The inner tube 48 extends through the center of the inflatable sleeve 50, and continues distal to the inflatable sleeve 50 as the fenestrated catheter 60. In the present embodiment, the fenestrated catheter 60 contains a plurality of fenestrations 65, and terminates in a blunted, sealed distal catheter tip 70.

Figure 4:
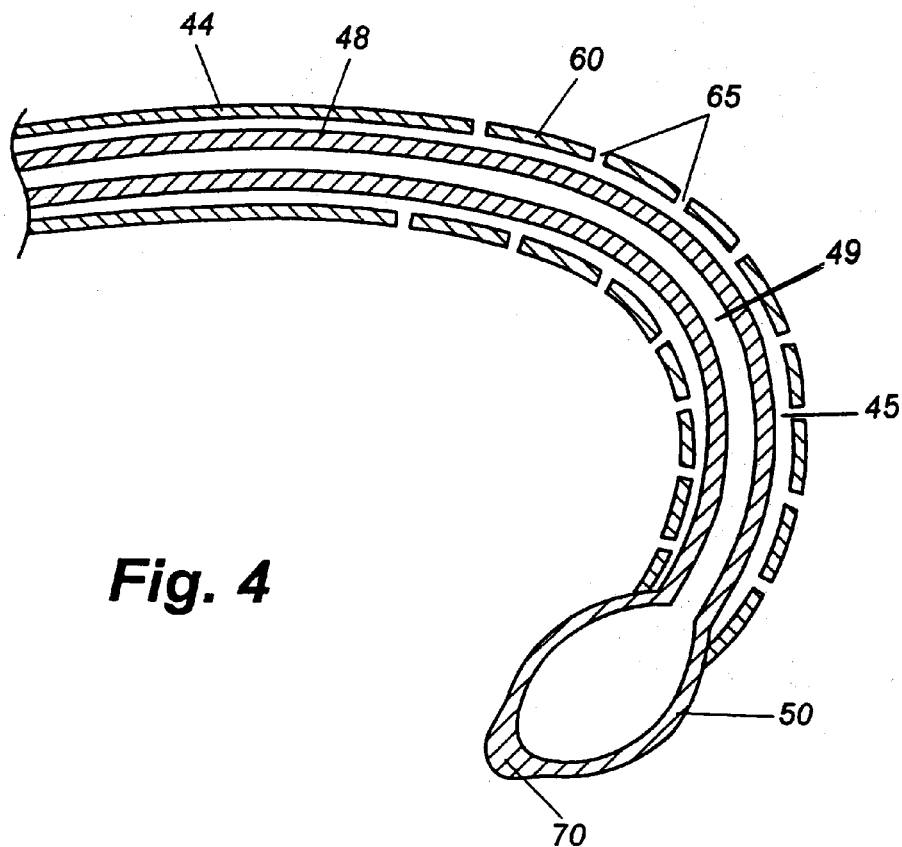
FIG. 4 is an illustration showing another possible embodiment of the inventive catheter in which the inflatable sleeve is operated by the internal lumen, and with the external lumen extending to the origin of the inflatable sleeve and containing a plurality of fenestrations.

In an alternate embodiment of the present invention, as shown in FIG. 4, the inflatable sleeve 50 is continuous as a terminal extension of the inner tube 48, and the device terminates in a blunted distal catheter tip 70 just distal to the inflatable sleeve 50. In this embodiment of the present invention, the outer tube 44 is continuous with the fenestrated catheter 60 terminally, such that the fenestrations 65 communicate with the outer lumen 45. In this embodiment, the inflatable sleeve 50 is controlled through the inner lumen 49, which is in continuous communication with the lumen of the inflatable sleeve 50. Any materials intended to be injected into Schlemm's canal are introduced through the outer lumen 45, and pass through the fenestrations 65 into Schlemm's canal proximal to the inflatable sleeve 50.

Figure 5:
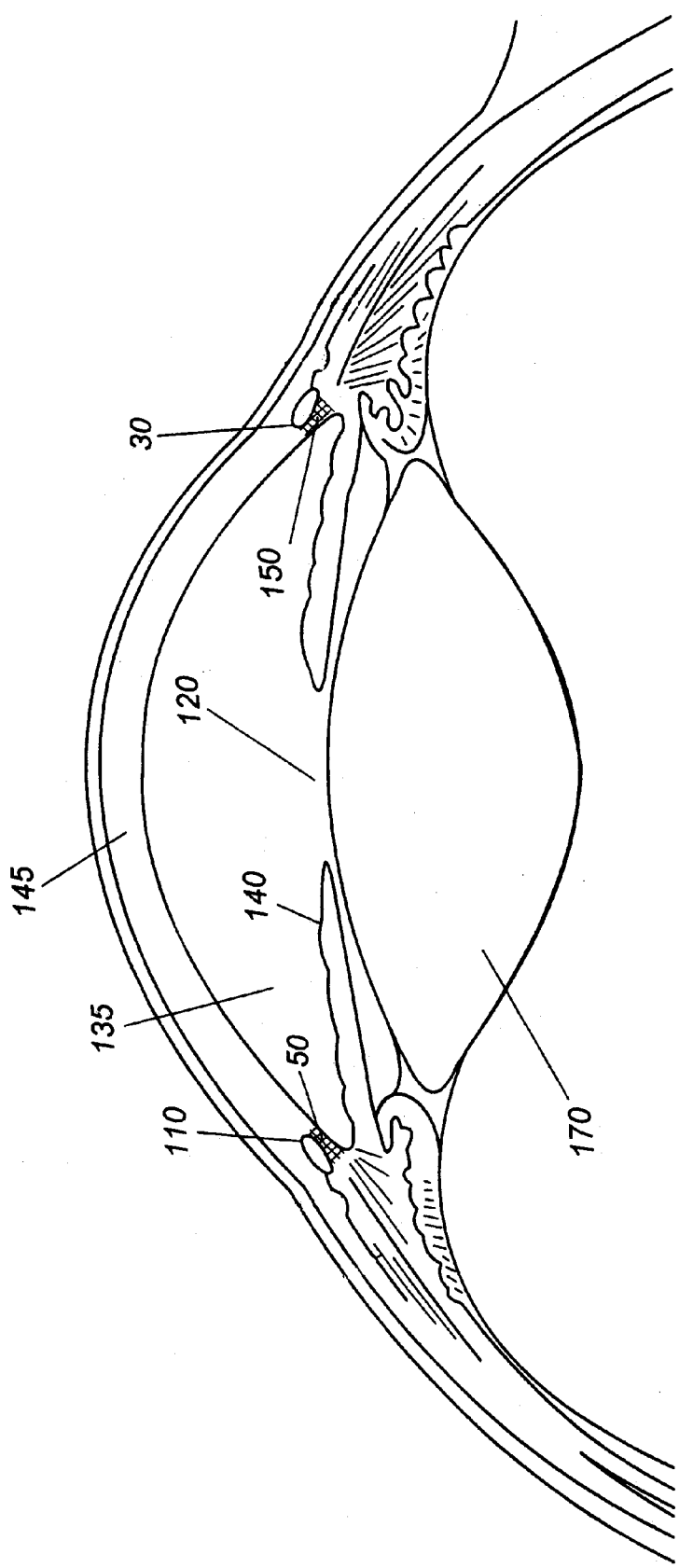
FIG. 5 is an illustration showing the relevant anatomic details of the human eye.

The surgical anatomy relevant to the present invention is illustrated in FIG. 5. Generally, FIG. 5 shows Schlemm's canal 110 and the pupil 120, with the anatomic relationship of those structures to the anterior chamber 135, the iris 140, cornea 145, trabecular meshwork 150, and lens 170.

Figure 6:
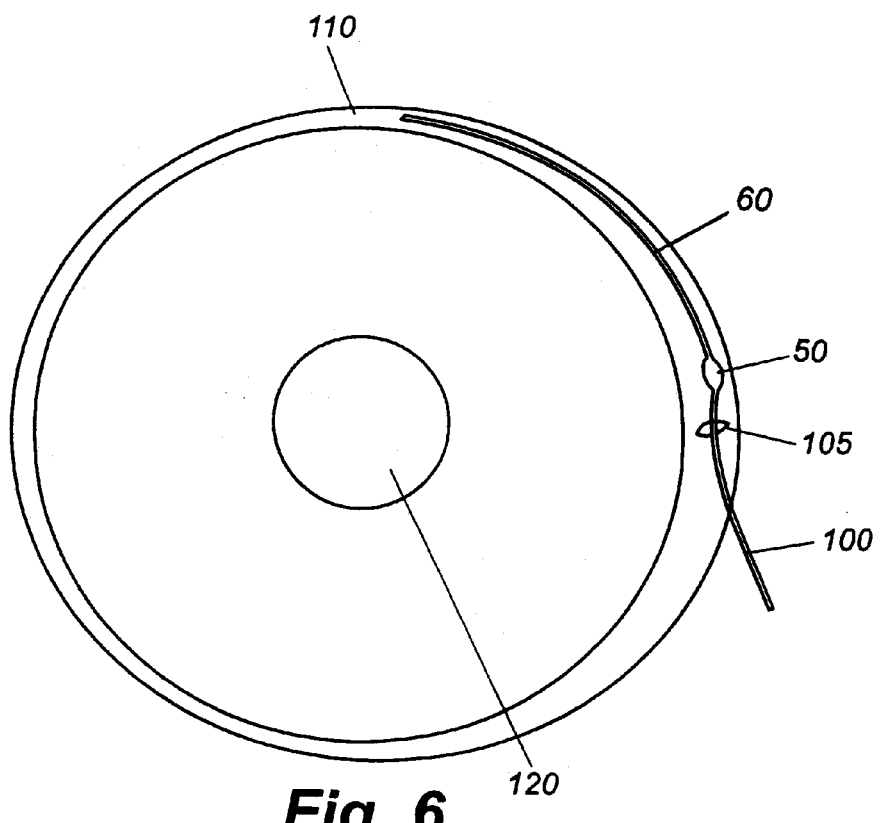
FIG. 6 is an illustration showing the anatomic relationships of the surgical placement of an exemplary embodiment of the present invention within Schlemm's canal.
Figure 7:
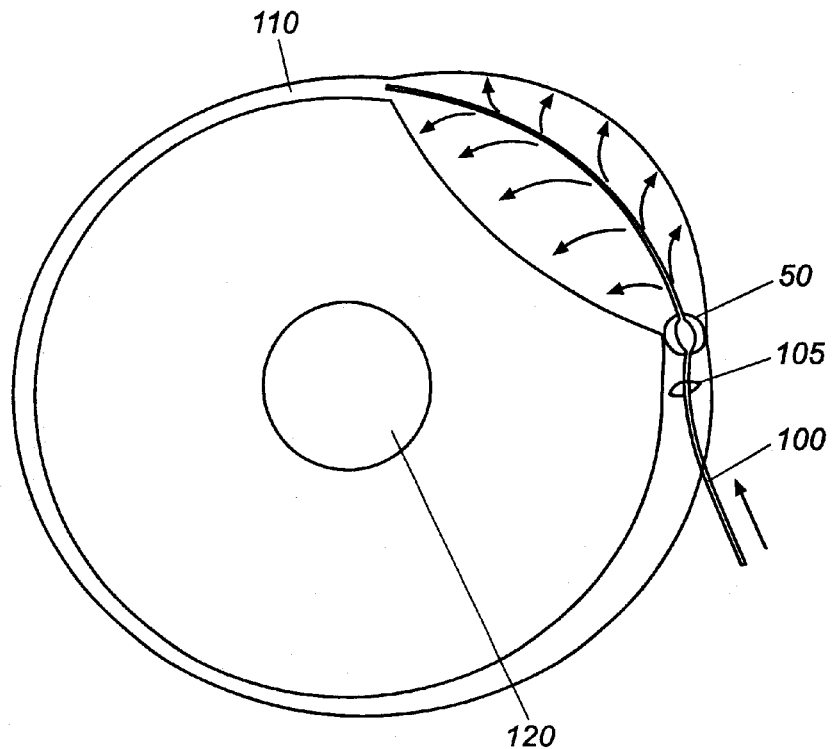
FIG. 7 is a schematic illustration showing the effects on Schlemm's canal (exaggerated for purposes of this illustration) of injection of a medicament by one embodiment of the inventive catheter.
Figure 8:
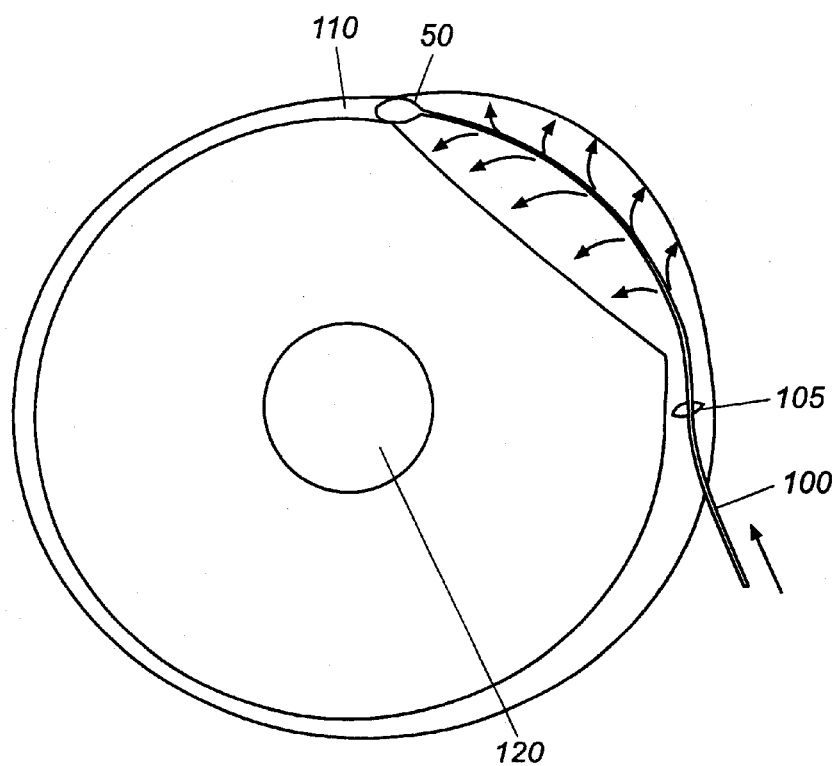
FIG. 8 is a schematic illustration showing the effects on Schlemm's canal (exaggerated for purposes of this illustration) of injection of a medicament by one embodiment of the inventive catheter.

The surgical placement and functionality of the present invention is shown from a frontal perspective in FIGS. 6–8. FIG. 6 shows the use of an embodiment like that shown in FIG. 3, in which the inflatable sleeve 50 is proximal to the fenestrated catheter 60. The distal portion 40 of the device is threaded into Schlemm's canal 110 through a surgical incision 105, such that the inflatable sleeve 50 is entirely received into the canal 110.

The guidewire 71 may be used during surgical placement of the device to afford temporary rigidity to the device to facilitate its placement. Once placement is achieved, the guidewire 71 may be withdrawn, leaving the device 100 in the desired anatomic position.

Once the distal portion 40 of the catheter is satisfactorily placed within Schlemm's canal 110, the inflatable sleeve 50 is inflated by an injection of liquid material or air through the outer lumen 45 of the catheter. The inflation of the inflatable sleeve 50 serves to seal Schlemm's canal 110. Subsequent injection of a desired material through the inner lumen 49 of the catheter is expressed through the fenestrated catheter 60, causing local expansion of Schlemm's canal 110 distal to the inflatable sleeve 50.

FIG. 8 shows the functionality of an embodiment like that shown previously in FIG. 4, in which the inflatable sleeve 50 is located terminally, and the fenestrations 65 are in the wall of the outer tube 44 towards the catheter tip. When the inflatable sleeve 50 is inflated by injection into the inner tube 48, Schlemm's canal 110 is effectively sealed distal to the inflated sleeve 50. Subsequent injection of a desired material through the outer lumen 45 of the catheter is expressed through the fenestrated catheter 60, causing local expansion of Schlemm's canal 110 proximal to the inflatable sleeve 50.

The surgical procedure necessary to insert the device requires an approach through a fornix-based conjunctival flap. A partial thickness scleral flap is then created and dissected half-thickness into clear cornea. A radial incision is made at the limbus beneath the scleral flap and deepened until Schlemm's canal is entered posteriorly. The anterior chamber may be deepened with injection of a viscoelastic and a miotic agent. The distal portion of the catheter device is grasped and threaded into Schlemm's canal. At the desired position, the catheter device is inflated to expand Schlemm's canal. The device is then deflated and withdrawn. The scleral flap and conjunctival wound are closed in a conventional manner.

While the above-described embodiments are exemplary, the invention contemplates a wide variety of shapes and configurations of the catheter to provide fluid communication between the anterior chamber and Schlemm's canal. The above-described embodiments are therefore not intended to be limiting to the scope of the claims and equivalents thereof.

What is claimed is:

1. A catheter device comprising a proximal portion manually controllable by a user, a distal portion sized and shaped for circumferential insertion into a portion of Schlemm's canal, and an inflation supply lumen extending from the proximal portion to the distal portion, wherein the distal portion of the inflation supply lumen is expandable and moves between a first position for insertion within Schlemm's canal and a second position for expansion of Schlemm's canal.

2. The catheter device of claim 1, further comprising a guiding lumen extending from the proximal portion to the distal portion, wherein the guiding lumen contains a steerable guidewire for directing the catheter device into a desired length of Schlemm's canal.

3. The catheter device of claim 1, wherein the distal portion has a diameter of about 0.1 to 0.5 mm.

4. The catheter device of claim 1, wherein the distal portion has a diameter of about 0.3 mm.

5. The catheter device of claim 1, wherein the distal portion has a length of about 1.0 to 20.0 mm.

6. The catheter device of claim 1, wherein the distal portion has a pre-formed curvature having a radius which approximates the radius of Schlemm's canal of a human eye.

7. The catheter device of claim 1, wherein the distal portion has a pre-formed curvature having a radius of between about 3 mm and 10 mm.

8. The catheter device of claim 1, wherein the distal portion has a pre-formed curvature having a radius of about 6 mm.

9. A method for the surgical treatment of glaucoma and other diseases, comprising inserting the catheter device of claim 1 into Schlemm's canal and expanding the canal by inflating the distal portion of the inflation lumen.

10. A catheter device comprising a proximal portion manually controllable by a user; a distal portion sized and shaped for circumferential insertion into a portion of Schlemm's canal; a medicament delivery lumen extending from the proximal portion to the distal portion, wherein the medicament delivery lumen has at least one fenestration therein on the distal portion for the delivery of medicaments into Schlemm's canal; and an inflation supply lumen extending from the proximal portion to the distal portion, wherein the distal portion of the inflation supply lumen is expandable and moves between a first position for insertion within Schlemm's canal and a second position for expansion of Schlemm's canal.

11. The catheter device of claim 10, further comprising a guiding lumen extending from the proximal portion to the distal portion, wherein the guiding lumen contains a steerable guidewire for directing the catheter device into a desired length of Schlemm's canal.

12. The catheter device of claim 10, wherein the distal portion has a diameter of about 0.1 to 0.5 mm.

13. The catheter device of claim 10, wherein the distal portion has a diameter of about 0.3 mm.

14. The catheter device of claim 10, wherein the distal portion has a length of about 1.0 to 20.0 mm.

15. The catheter device of claim 10, wherein the distal portion has a pre-formed curvature having a radius which approximates the radius of Schlemm's canal of a human eye.

16. The catheter device of claim 10, wherein the distal portion has a pre-formed curvature having a radius of between about 3 mm and 10 mm.

17. The catheter device of claim 10, wherein the distal portion has a pre-formed curvature having a radius of about 6 mm.

18. A method for the surgical treatment of glaucoma and other diseases, comprising inserting the catheter device of claim 10 into Schlemm's canal and delivering a medicament into the canal through the at least one fenestration in the distal portion of the medicament delivery lumen.

* * * * *

UNITED STATES PATENT AND TRADEMARK OFFICE
CERTIFICATE OF CORRECTION

PATENT NO. : 6,524,275 B1
DATED : February 25, 2003
INVENTOR(S) : Lynch et al.

It is certified that error appears in the above-identified patent and that said Letters Patent is hereby corrected as shown below:

<u>Title page,</u>
After Item [60], Related U.S. Application Data, please add the following government license:
-- Government License
The U.S. Government has reserved a nonexclusive, irrevocable, royalty-free license in the invention with power to grant licenses for all government purposes. --

Signed and Sealed this

Twenty-second Day of June, 2004

JON W. DUDAS
*Acting Director of the United States Patent and Trademark Office*